United States Patent [19]
Nicas et al.

[11] Patent Number: 5,994,297
[45] Date of Patent: Nov. 30, 1999

[54] THERAPY FOR *STAPHYLOCOCCUS AUREUS*

[75] Inventors: Thalia Ioanna Nicas, Indianapolis; David Albert Preston, Carmel; Michael Lee Zeckel, Zionsville, all of Ind.

[73] Assignee: Eli Lilly and Company, Indianapolis, Ind.

[21] Appl. No.: 09/116,025

[22] Filed: Jul. 15, 1998

Related U.S. Application Data

[60] Provisional application No. 60/056,712, Aug. 22, 1997.
[51] Int. Cl.$^6$ .......................... A61K 38/12; A61K 38/14; C07K 9/00
[52] U.S. Cl. ........................................ 514/8; 514/9; 514/2
[58] Field of Search .............................................. 514/8, 9

[56] References Cited

FOREIGN PATENT DOCUMENTS 0 667 353 A1  1/1995  European Pat. Off. .

OTHER PUBLICATIONS

Abstracts of the 37hu th ICAAC, C–164, Sep. 28–Oct. 1, 1997, p. 74.

J. Antimicrob Chemother, Hiramatsu et al, 1997; 40:135–136.

Ann Intern Med., M.B. Edmond et al, 1996; 124:329–334.

FEMS Microbiology Letters, Noble et al, 93 (1992) 195–198.

New England J. Medicine, Schwalbe et al, 1987, vol. 316, No. 15, pp. 927–931.

J. Clin Microbiol., Veach et al, Sep. 1990, vol. 28, No. 9, pp. 2064–2068.

The Lancet, Jan. 5, 1991, vol. 337, p. 54.

Exp. Opin. Ther. Patents 6(1), 73–75 (1996).

Jones, Ronald N., et al., Antimicrobial Agents and Chemotherapy, 41(2), 488–493 (1996).

Biavasco, Francesca, et al., Antimicrobial Agents and Chemotherapy, 41(10), 2165–2172 (1997).

Primary Examiner—Michael P. Woodward
Assistant Examiner—Michael Borin
Attorney, Agent, or Firm—Arlene K. Musser

[57] ABSTRACT

The present invention is directed to methods for treating infections caused by *Staphylococcus aureus* with reduced glycopeptide sensitivity. The invention is preferably practiced with strains of *Staphylococcus aureus* which are methicillin resistant, such as the Mu5O strain.

3 Claims, No Drawings

THERAPY FOR *STAPHYLOCOCCUS AUREUS*

CROSS-REFERENCE TO RELATED APPLICATIONS

This application claims priority to provisional application Serial No. 60/056,712 dated Aug. 22, 1997.

BACKGROUND OF THE INVENTION

Infectious diseases have historically taken a tremendous toll of human life. In this century, many of these have been controlled by various antibacterials. However, bacteria have the ability to mutate, and by this technique, have in numerous cases become resistant to the very antibacterials which hitherto have been efficacious in controlling them.

As an example, the glycopeptide vancomycin has been used for the control of infections due to gram-positive bacterial organisms, including *Enterococcus* species and *Staphylococcus* species, for nearly four decades. Another glycopeptide, teicoplanin, has been introduced more recently, also for the control of gram-positive bacterial organisms. Quite recently, however, bacterial strains have arisen which are less sensitive to these glycopeptides. These strains may be of only reduced sensitivity, or in some cases they are completely resistant and the glycopeptides are of no avail.

Therefore, there is a need for new methods of therapy to treat infections due to bacterial strains of reduced sensitivity or resistance.

BRIEF SUMMARY OF THE INVENTION

The present invention is directed to methods for the control of strains of *Staphylococcus aureus* which are of reduced sensitivity to glycopeptides. These methods employ the compound $N^{DISACC}$-(4-(4-chlorophenyl)benzyl)A82846B, or a pharmaceutically acceptable salt thereof.

DETAILED DESCRIPTION OF THE INVENTION

In the present invention, $N^{DISACC}$-(4-(4-chlorophenyl)benzyl)A82846B, or a pharmaceutically acceptable salt thereof, is used to treat host animals suffering a bacterial infection attributable to a strain of *Staphylococcus aureus* which is of reduced glycopeptide sensitivity. $N^{DISACC}$-(4-(4-chlorophenyl)benzyl)A82846B and salts thereof are described in published EPO 0667353, which is incorporated herein by reference. See Example 229.

"Reduced sensitivity" describes the phenomenon of a bacterium which requires elevated MIC (minimum inhibitory concentration) for efficacy, as compared to normal bacteria controlled at lower MICs. MICs are determined by standard in vitro testing methods (Methods for Dilution Antimicrobial Susceptibility Tests for Bacteria That Grow Aerobically—Fourth Edition. Approved Standard, M7–A4, published by National Committee for Clinical Laboratory Standards, 1997). "Reduced sensitivity" is defined by the NCCLS as an MIC of 8 mg/L or higher for vancomycin and an MIC of 16 mg/L or higher for teicoplanin.

The term "reduced glycopeptide sensitivity" includes outright resistance, which is defined by NCCLS as an MIC of 32 mg/L or higher, for either vancomycin or teicoplanin. An example of a strain for which the present methods are intended is the strain of *Staphylococcus aureus* which is announced by Hiramatsu et al. in *J. of Antimicrobial Chemotherapy*, 1997, 40, 135–146. This strain, named "Mu50," is described as having a vancomycin MIC of 8 mg/L.

The term "reduced glycopeptide sensitivity" means reduced sensitivity to either vancomycin or teicoplanin, or reduced sensitivity to both. The term also includes strains which are simultaneously of reduced sensitivity to antibacterials other than the glycopeptides, such as the penicillin type of antibacterials. In a preferred embodiment, the present invention is directed to the control of *Staphylococcus aureus* which is not only of reduced sensitivity to the glycopeptides, but which is also methicillin resistant ("MRSA"). The above referenced Hiramatsu strain is an example.

Bacterial mechanisms which confer reduced sensitivity, including resistance, are legion. The present invention is particularly directed to those strains in which the reduced glycopeptide resistance is attributable to other than Van A genes and/or Van B genes, known as "Van A and Van B negative strains."

The present invention is practiced in the usual mode of antibacterial therapy. The subject compound or a salt thereof is administered to the host animal. The compound can sometimes be successfully administered on a single occasion, but is more commonly administered at intervals over a period of days to assure control. Administration can be by the oral route or by a parenteral route; intravenous infusion is generally a preferred route of administration.

The exact dose to be employed is not critical, and will vary with the host, the particular strain, and other factors known to the clinician. The dose must be high enough to ensure adequate concentration of the compound in the host's tissues. In general, doses of from about 1 mg/kg to about 25 mg/kg are efficacious in the present invention; preferred doses are from about 1.5 mg/kg/day to about 5 mg/kg/day. A typical daily dose for an adult human is from about 100 mg to about 500 mg.

In the normal practice of pharmaceuticals, the compound to be employed in the present invention is preferably formulated with one or more adjuvants, carriers, and/or diluents. The identity of suitable such components is well known to those skilled in the art, as is the method of mixing such components. For oral administration, the subject compound can be formulated as a capsule, tablet, suspension, or other form for oral delivery. For intravenous infusion, the compound can be dissolved in a suitable intravenous fluid, such as physiological saline, 5% dextrose solution, or the like.

We claim:

1. A method of treating an infectious disease in a warm blooded animal, which disease is attributable to a strain of *Staphylococcus aureus* which (1) has reduced sensitivity to either vancomycin or teicoplanin or reduced sensitivity to both vancomycin and teicoplanin, (2) is resistant to methicillin, and (3) is Van A and Van B negative, which method comprises administering to the animal an effective amount of $N^{DISACC}$-4-(4-chlorophenyl)benzyl)A82846B or a salt thereof.

2. A method of claim 1 in which the strain of *Staphylococcus aureus* is resistant to vancomycin or teicoplanin.

3. A method of claim 1 in which the strain of *Staphylococcus aureus* is Mu5O.

* * * * *